United States Patent [19]

Antoni et al.

[11] Patent Number: 4,552,864

[45] Date of Patent: Nov. 12, 1985

[54] GONADOLIBERIN DERIVATIVES PROCESS FOR THE PREPARATION AND PHARMACEUTICAL COMPOSITIONS THEREOF

[75] Inventors: Ferenc Antoni; Judit Erchegyi; Anikó Horváth; Györgi Kéri; Imre Mezö; Károly Nikolics; János Seprödi; András Széll; Balázs Szökè; István Teplán, all of Budapest, Hungary

[73] Assignee: Reanal Finomvegyszergyar, Budapest, Hungary

[21] Appl. No.: 608,261

[22] PCT Filed: May 25, 1983

[86] PCT No.: PCT/HU83/00028

§ 371 Date: Jan. 11, 1984

§ 102(e) Date: Jan. 11, 1984

[87] PCT Pub. No.: WO83/04250

PCT Pub. Date: Dec. 8, 1983

Related U.S. Application Data

[63] Continuation of Ser. No. 576,396, Jan. 11, 1984, abandoned.

[30] Foreign Application Priority Data

May 25, 1982 [HU] Hungary .................................. 1692

[51] Int. Cl.$^4$ ..................... A61K 37/00; C07C 103/52
[52] U.S. Cl. ..................... 514/15; 514/800; 260/112.5 LH
[58] Field of Search ............... 260/112.5 LH; 514/15, 514/800

[56] References Cited

U.S. PATENT DOCUMENTS

| | | | |
|---|---|---|---|
| 3,888,836 | 6/1975 | Veber et al. | 260/112.5 LH |
| 4,024,248 | 5/1977 | Konig et al. | 260/112.5 LH |
| 4,382,922 | 5/1983 | Rivier et al. | 260/112.5 LH |
| 4,410,514 | 10/1983 | Vale, Jr. et al. | 260/112.5 LH |

FOREIGN PATENT DOCUMENTS 2347151  9/1972  Fed. Rep. of Germany ... 260/112.5 LH

OTHER PUBLICATIONS

Biochem. And Biophys. Res. Commun., 60, (1974), 406–412.

*Primary Examiner*—Delbert R. Phillips
*Attorney, Agent, or Firm*—Karl F. Ross; Herbert Dubno

[57] ABSTRACT

The invention relates to new gonadoliberin derivatives of the formula (I)

Glp-His-Trp-Ser-Tyr-X-Leu-Arg-Pro-Y,    (I)

wherein

Y represents a glycine-amide group or an -NH-alkyl group having 1 to 4 carbon atoms in the alkyl moiety, X stands for a D-thyroxyl, D-thyronyl or D-4-chlorophenylalanyl group, and acid addition salts and metal complexes thereof.

The new nona- and decapeptide derivatives have an excellent luteinizing and folliculus stimulating hormone releasing activity, and they can therefore be used as active ingredients in pharmaceutical compositions for human or veterinary application.

6 Claims, No Drawings

GONADOLIBERIN DERIVATIVES PROCESS FOR THE PREPARATION AND PHARMACEUTICAL COMPOSITIONS THEREOF

CROSS REFERENCE TO RELATED APPLICATIONS

This application is a continuation of copending U.S. application Ser. No. 576,396 filed Jan. 11, 1984, now abandoned.

FIELD OF THE INVENTION

This invention relates to new gonadoliberin derivatives and a process for their preparation. More particularly, the invention concerns new gonadoliberin derivatives of the formula (I)

Glp-His-Trp-Ser-Tyr-X-Leu-Arg-Pro-Y    (I)

wherein
X represents a D-4-chlorophenyl-alanyl, D-thyroxyl or D-thyronyl group and
Y is a glycine amide or —NH-alkyl group, having 1 to 4 carbon atoms in the alkyl moiety,
and acid addition salts and metal complexes thereof. The invention also includes a process for the preparation of said nona- or decapeptide derivatives and pharmaceutical or veterinary compositions containing them.

The abbreviations used in the above formula and hereinbelow correspond to the generally accepted nomenclature of the chemistry of peptides [see e.g. *J. Biol. Chem.* 241, 527 (1966)]. In the specification the following further abbreviations will be used:
Cpa=4-chlorophenyl-alanine
Thy=thyronine
Thx=thyroxine

BACKGROUND OF THE INVENTION

Gonadoliberin (also referred to as gonadotropin releasing hormone, Gn-RH, luteinizing and folliculus stimulating hormone, releasing hormone, LH(FSH-RH) and its known derivatives are capable of releasing the luteinizing and folliculus stimulating hormones (LH and FSH).

It is known in the art [M. Monahan et al., *Biochemistry* 12, 4616–4620 (1973)] that those gonadoliberin derivatives in which glycine in the 6-position is replaced by certain D-amino acids have a surplus effect related to gonadoliberin. This increase in the activity is most expressed in case of the compounds which contain D-tryptophane or D-tert.butyl-serine in the 6-position (J. Sandow et al., *Control of Ovulation*, Butterworths, London, 1978, pp. 49–70).

According to Nestor et al.[*J. Med. Chem.* 25, 795–801 (1982), U.S. Pat. No. 4,234,571] by replacing the glycine in the 6-position of gonadoliberin by D-amino acids having a highly lipophilic side-chain also effective gonadoliberin analogues can be prepared.

It is further known that the biological activity of gonadoliberin can further be increased by replacing the glycine-amide group in the 10-position with amide groups containing aliphatic carbon chain [M. Fujino et al., *J.Med.Chem.* 16, 1144–1147 (1973)].

According to Coy, D. H., Labrie, F., Savary, M., Coy, E. J., Schally, A. V. *Biochem. Biophys. Res. Commun.* 67, 576–582 (1975), potent gonadoliberin derivatives can be obtained also by replacing the 6-glycine in gonadoliberin or in a corresponding amide by a D-phenylalanyl group.

The invention relates to new gonadoliberin derivatives which show a better biological activity than their known analogues.

According to another aspect of the invention we provide a process for the preparation of the new nona- and decapeptide derivatives of the formula (I) (X and Y are as defined above), by which in place of the 6-glycine group other amino acids can be incorporated with a good yield, without racemization.

SUMMARY OF THE INVENTION

The invention is based on the surprising finding that the compounds which contain a D-thyroxyl, D-thyronyl or D-4-chlorophenyl-alanyl group in place of the 6-glycine group of gonadoliberin have a better biological activity and can easily be prepared.

We have further found that the activity of these new gonadoliberin derivatives can be increased further by replacing the glycine-amide group in the 10-position by an —NH—$C_{1-4}$-alkyl group.

According to the invention the new nona- or decapeptide derivatives of the formula (I)

Glp-His-Trp-Ser-Tyr-X-Leu-Arg-Pro-Y    (I)

wherein X and Y have the same meaning as defined above, and acid addition salts and complexes thereof are prepared by condensing a pentapeptide azide of the formula (II)

Glp-His-Trp-Ser-Tyr-N$_3$    (II)

with a tetra- or pentapeptide of the formula (III)

X-Leu-Arg-Pro-Y    (III)

wherein X and Y are as defined above, and if desired, converting the nona- or decapeptide amide obtained into an acid addition salt thereof by reacting it with a suitable acid, or if desired, deliberating the free base from an acid addition salt obtained with a base, and if desired, converting a nona- or decapeptide-amide obtained into a metal complex thereof.

BEST MODE FOR CARRYING OUT THE INVENTION

The D-Thy$^6$-gonadoliberin derivatives are preferably prepared by reducing the D-Thx$^6$-gonadoliberin derivatives. The reduction is preferably carried out with hydrogen. If the reduction is performed with tritium gas, in the presence of a catalyst, from D-Thx$^6$-gonadoliberin D-Thy$^6$-gonadoliberin specifically labelled with tritium is obtained. These gonadoliberin derivatives which show a high specific radioactivity can excellently be used in various tests and as diagnostics.

The pentapeptide component of the formula (II) is preferably prepared by the condensation of pyroglutamyl-histidyltryptophane-azide and seryltyrosine methylester. By this method the undesired racemization can be avoided. Pyroglutamylhistidyl-tryptophane used as a starting compound can be prepared by coupling pyroglutamic acid with (N-imidazol-dinitrophenyl)-histidyltryptophane methylester.

The tetra- or pentapeptides of the formula (III) are preferably prepared by acylating a tri- or tetrapeptide of the formula Leu-Arg-Pro-Y (Y is as defined above)

known in the art [N. Yanaihara et al., *J.Med.Chem.* 16, 373 (1973)] on its amino group with an X amino acid supplied with a Boc or Z protecting group (X is as defined above) by a method conventionally used in peptide chemistry.

The LH-releasing activity of the new peptides according to the invention was tested by the following method, in which for comparison the known gonadoliberin was employed under the same conditions.

The adenohypophysis of female Sprague-Dawley rats weighing 150–200 g each was eliminated and pretrypsinized. Approximately 40–50 pituitaries were placed into separate flasks and allowed to stand in 25 ml of a 0.25% trypsin solution (Sigma, type 111) at 0° to 4° C. for 16 hours. The pituitaries were then stirred under a 5% $CO_2$ atmosphere at 37° C. for 20–25 minutes while they were decomposed to their cells. To the cell suspension soya-bean trypsin inhibitor was added whereupon it was suspended and centrifuged in a Medium 199 solution (with Earle's salts, Flow Laboratories, UK) three times (800 x g, 10 minutes). The cell suspension was padded through a sterile metal filter and the number of cells in one ml was counted. After counting, 3 ml of the cell suspension was dispensed into culture flasks each containing $1.8 \times 10^6$ cells. The cells were cultured for 3 days at 37° C. under a 5% $CO_2$ atmosphere. On the 3rd day the medium was replaced by a fresh one and incubation was continued for one more day. On the 4th day the medium was changed again and a medium containing a $10^{-7}$ to $10^{-12}$ molar solution of the peptides to be tested was added to the cell cultures. The cells were incubated with the peptide solutions for 4 hours, the culture solutions were eliminated and the amount of the LH-hormone released from the cells was determined by radioimunoassay. For the various peptides the following $ED_{50}$-values and relative activities were obtained.

| GnRH | 0.3433 M | 1.00 |
|---|---|---|
| D-Cpa$^6$-GnRH | 0.02063 nM | 16.6 |
| D-Thx$^6$-GnRH | 0.02892 nM | 11.9 |
| D-Thy$^6$-GnRH | 0.02435 nM | 14.1 |
| D-Cpa$^6$-GnRH-EA | 0.01278 nM | 26.9 | wherein
Cpa: 4-chlorophenylalanine
EA: ethylamide [GnRH-(1-9)-ethylamide]

According to a still further aspect of the invention there are provided human or veterinary pharmaceutical compositions, which are generally prepared by admixing at least one compound of the formula (I) or a pharmaceutically acceptable salt or complex thereof with carriers conventionally used in the preparation of pharmaceutical compositions and formulating the compositions obtained for example as tablets, dragées, capsules, suppositories, injection solutions, nasal spray, etc.

In the veterinary therapy the peptides of the formula (I) can effectively be used for example as anoestronic or anovulatory agents or for treating follicular cysts. They are generally administered in a single daily dose of 5–200 µg, preferably 50–100 µg, intramuscularly, subcutaneously or intravenously. When applying against follicular cysts a repeated treatment is also possible. They are effective in the treatment of various animals, e.g. cattle.

In the human therapy the new compounds according to the invention proved to be effective contraceptives. For this purpose they are generally administered in a single 400 to 600 µg/day dose as a nasal spray. The new compounds are further effective in treating mammary carcinoma or cancer of the prostate. In this application their daily dose generally is 5 to 50 µg when administered subcutaneously, and 400 to 600 µg when a nasal spray is employed. The pharmaceutical compositions containing the new peptides of the formula (I) as an active ingredient can be formulated and administered also as injection solutions or suppositories. The new peptides are effective also against cryptorchidism.

The main advantages of the process according to the invention and the new peptides obtained by this process are as follows:

(a) The new gonadoliberin derivatives according to the invention are more active than those known in the art.

(b) The pentapeptides of the formula (II) are common intermediates of the preparation of all end products.

(c) The X amino acids are incorporated into the peptides in the last step of the preparation of the tetra- or pentapeptides of the formula (III), therefore the replacement of the 6-amino acid, which plays the most important role in the biological activity, takes place easily, in a simple way and the undesired racemization can be avoided.

(d) The D-Thy$^6$-gonadoliberin derivatives can be effectively labelled with tritium, and the derivatives obtained which have a high specific radioactivity can very advantageously be used in pharmacological, pharmakinetical, biochemical and physiological assays or as diagnostics.

Further details of our invention are illustrated by the following non-limiting Examples. In the Examples the melting points are indicated in °C., the values are not corrected.

The thin layer chromatographic $R_f$-values were determined on Kieselgel (DC, Alufolien, Merck) plates, using the following solvent mixtures:

1. Ethyl acetate/pyridine/acetic acid/water 30:20:6:11
2. ethyl acetate/pyridine/acetic acid/water 60:20:6:11
3. ethyl acetate/pyridine/acetic acid/water 120:20:6:11
4. ethyl acetate/pyridine/acetic acid/water 240:20:6:11
5. acetone/toluene 1:1
6. chloroform/methanol/acetic acid 85:10:5
7. methylethyl ketone/pyridine/water 65:15:20
8. n-butanol/acetic acid/water/ethyl acetate 1:1:1:1
9. n-butanol/acetic acid/water 4:1:1
10. n-butanol/acetic acid/water 4:1:5 (upper phase)
11. n-butanol/pyridine/acetic acid/water 15:1:4:20 (upper phase)
12. i-propanol/1M acetic acid 2:1

EXAMPLE 1

Preparation of D-Cpa$^6$-gonadoliberin (a) BOC-His(DNP)-trp-OMe
M: 622.62.

21.12 g (50 mmoles) of BOC-His(DNP)-OH are dissolved in 100 ml of dimethyl formamide and the solution is cooled to 0° C. Thereafter 10.32 g (50 mmoles) of dicyclohexyl-carbodiimide and 7.66 g (50 mmoles) of N-hydroxy-benztriazole are added with stirring. The mixture is stirred at 0° C. for 10 minutes and the precipitated dicyclohexyl-urea is filtered off.

12.74 g (50 mmoles) of H-Trp-OMe.HCl are dissolved in 70 ml of dimethyl formamide and the solution is cooled to 0° C. 6.93 ml (50 mmoles) of triethyl amide are added and the precipitated triethylamine hydrochloride is filtered off after stirring for 5 minutes.

The two solutions are combined and stirred at 0° C. overnight. Thereafter the precipitated DCU is filtered off and the solution is evaporated to dryness. The oily residue is dissolved in 500 ml of ethyl acetate and shaken with three 100-ml portions of ice cool 1M KHSO$_4$ solution, five 100-ml portions of a saturated NaHCO$_3$ solution and finally with two 100-ml portions of a 10% NaCl solution. The organic phase is dried over magnesium sulfate, filtered and evaporated to dryness. The obtained oily substance is powdered with petroleum ether, filtered and dried. The crystalline product obtained can be recrystallized from ethyl acetate with petroleum ether.

Yield: 27.70 g (89%).
Melting point: 119° to 122° C.
$[\alpha]_D^{22} = +14.1°$ (c=1, DMF).
$R_f^4 = 0.62$; $R_f^5 = 0.41$.

(b) H-His(DNP)-Trp-OMe.2HCl
M: 522.49 (free base); 595.41 (.2HCl).

24.9 g (40 mmoles) of BOC-His(DNP)-OMe dipeptide are dissolved in 100 ml of methanol and 100 ml of a 4 n methanolic hydrochloric acid solution are added. The mixture is allowed to stand at room temperature for 30 minutes, while the dipeptide ester hydrochloride is crystallized. The crystals are filtered off, washed with ether and dried.

Yield: 21.91 g (92%).
Melting point: 198° to 202° C.
$[\alpha]_D^{22} = 0.49°$ (c=1, DMF).
$R_f^3 = 0.46$; $R_f^4 = 0.18$; $R_f^5 = 0.06$.

(c) Glp-His-(DNP)-Trp-OMe
M: 633.60.

4.85 g (36.8 mmoles) of L-pyroglutamic acid, 7.58 g of dicyclohexyl-carbodiimide and 5.63 g of N-hydroxybenztriazole are dissolved in 100 ml of dimethyl formamide. The mixture is stirred at 5° to 10° C. for 10 minutes whereupon the precipitated DCU is filtered off.

20.84 g (35 mmoles) of H-His(DNP)-Trp-OMe.2HCl are dissolved in 100 ml of dimethyl formamide and 9.72 ml (70 mmoles) of triethyl amine are added to the solution. After stirring for 5 minutes the precipitated triethylamine hydrochloride is filtered off. The two solutions are combined and stirred at room temperature overnight. Thereafter 90 ml of acetone are added to the mixture and the precipitated insoluble material is filtered off. Evaporation of the solution affords an oily material, which is triturated with ethyl acetate, filtered and dried. The dry crystalline material is washed with three 25-ml portions of water and dried. The product can be recrystallized by dissolving in hot ethyl acetate and cooling.

Yield: 18.42 g (83.1%)
Melting point: 148° to 151° C.
$[\alpha]_D^{23} = +5.2°$ (c=1, DMF)
$R_f^3 = 0.53$; $R_f^4 = 0.38$ (d) Glp-His-Trp-OMe
M: 466.50.

15.84 g (25 mmoles) of Glp-His(DNP)-Trp-OMe protected tripeptide are dissolved in a mixture of 100 ml of dimethyl formamide and 40 ml of water. 4 ml of mercapto-ethanol are added and the pH of the solution is adjusted to 8 with triethyl amine. It is allowed to stand at room temperature for 30 minutes, and is evaporated to dryness in vacuo. The oil material is triturated with ether, filtered and dried. The product obtained is dissolved in a small portion of methanol and is recrystallized by adding ether. The precipitated crystals are filtered off and dried.

Yield: 10.92 g (93.6%).
Melting point: 228° to 232° C.
$[\alpha]_D^{22} = +4.04°$ (c=0.42, DMF).
$R_f^2 = 0.30$.

(e) Glp-His-Trp-N$_2$H$_3$
M: 466.51.

9.33 g (20 mmoles) of Glp-His-Trp-OMe tripeptide are dissolved in 250 ml of methanol. To the solution 20 ml of a 98% hydrazine hydrate are added. The reaction mixture is stirred at 40° C. for 3 hours and subsequently at room temperature overnight. The precipitated material is then filtered off, washed with cold methanol and dried.

Yield: 7.58 g (81.2%).
Melting point: 166° to 169° C.
$[\alpha]_D^{22} = -22.3°$ (c=0.5, DMF).
$R_f^1 = 0.50$; $R_f^2 = 0.14$.

(f) Glp-His-Trp-Ser-Tyr-OMe
M: 716.8.

7.0 g (15 mmoles) of Glp-His-Trp-N$_2$H$_3$ obtained in Step e/are dissolved in 60 ml of dimethyl formamide. The solution is cooled to 0° C. and 7.5 ml (45 mmoles) of a 6 n HCl solution are added with stirring. Thereafter 1.035 g (15 mmoles) of NaNO$_2$ are added to the mixture as a concentrated aqueous solution, dropwise, and the mixture is stirred at 0° C. for a further 15 minutes. To the reaction mixture a solution of 4.78 g (15 mmoles) of H-Ser-Tyr-OMe-HCl in 15 ml of dimethyl formamide are added. The pH is adjusted to neutral with 6.25 ml (45 mmoles) of triethyl amine and the mixture is stirred at 0° to 4° C. overnight. On the following day it is evaporated to dryness in vacuo and the oily product is triturated with ether.

12.1 g (100%) of the title compound are obtained, containing a small amount of impurity. This product can be converted into hydrazide without purification and the hydrazide obtained is readily crystallizable.

The physical properties of a control sample recrystallized from methanol:
Melting point: 188° to 190° C.
$[\alpha]_D^{22} = -3.48°$ (c=1, DMF).
$R_f^1 = 0.58$; $R_f^2 = 0.26$.

(g) Glp-His-Trp-Ser-Tyr-N$_2$H$_3$
M: 716.8.

12 g of crude, powdered Glp-His-Trp-Ser-Tyr-OMe pentapeptide ester are dissolved in 200 ml of methanol, 10 ml of a 98% hydrazine hydrate are added and the mixture is stirred at 40° C. for 3 hours. The mixture is stirred at room temperature overnight, whereupon the precipitated crystals are filtered off and dried in an exsiccator, over concentrated sulfuric acid. The dry crystalline material is dissolved in 250 ml of a 0.5 n hydrochloric acid solution, its pH is adjusted to 8 with saturated sodium carbonate solution, it is allowed to stand at 0° C. for 2 hours and the precipitated crystals are filtered, washed with ice cold water and dried.

Yield: 6.12 g (56.9% calculated for the two steps).
Melting point: 205° to 206° C.
$[\alpha]_D^{22} = 21.51°$ (c=1, DMF).
$R_f^1 = 0.39$; $R_f^2 = 0.14$.

Hydrazine nitrogen: found: 3.79%, 3.76%. theoretical: 3.91%.

(h) BOC-D-Cpa-OPFP
M: 465.8.

A solution of 6.0 g (20 mmoles) of BOC-D-Cpa-OH in 50 ml of ethyl acetate is cooled to 0° C. and 4.0 g (22 mmoles) of pentafluorophenol and subsequently 4.52 g (22 mmoles) of dicyclohexyl-carbodiimide are added. The precipitation of DCU starts immediately. The mixture is stirred at 0° C. for one hour and at 20° C. for a further one hour, whereupon the precipitated DCU is filtered off. The solution is evaporated in vacuo and the residue is crystallized from a mixture of ethyl acetate and petroleum ether. The substance is allowed to stand in a refrigerator whereupon it is filtered, washed with a 1:1 mixture of ethyl acetate and petroleum ether and dried.

Yield: 7.8 g (84%).
Melting point: 134° to 135° C.
$[\alpha]_D^{26} = +23°$ (c=1, MeOH).
$R_f^6 = 0.75$.

Analysis for $C_{20}H_{17}O_4NClF_5$: calculated: C 51.57%, H 3.67%, N 3.00%, Cl 7.61%. found: C 51.52%, H 3.66%, N 3.05%, Cl 7.58%.

(i) BOC-D-Cpa-Leu-Arg(NO₂)-Pro-Gly-NH₂
M: 767,28.

1.5 g. (2.5 mmoles) of H-Leu-Arg(NO₂)-Pro-Gly-NH₂ trifluoroacetate [N. Yamaihara et al., *J. Med. Chem.* 16, 373 (1973)] are dissolved in 15 ml. of dimethyl formamide. The solution is cooled to 0° C. and 1.16 g. (2.5 mmoles) of BOC-D-Cpa-OPFP activated ester are added. The reaction mixture is then neutralized with 5 mmoles of triethyl amine, and it is stirred at 0° C. for 30 minutes and at 20° C. for one hour. Dimethyl formamide is eliminated in vacuo, under 45° C. The residue is triturated with ether and then with water, filtered and dried.

Yield: 1.82 g. (95%).
Melting point: 134° to 135° C.
$R_f^2 = 0.8$; $R_f^3 = 0.5$; $R_f^6 = 0.5$.
Amino acid analysis: Cpa 1.05; Gly 1.00; Leu 1.02; Pro 0.92; Arg 0.95

(j) H-D-Cpa-Leu-Arg-Pro-Gly-NH₂.2HF
M: 662.15/2HF 300 mg (0.39 mmoles) of the pentapeptide prepared in Step (i) are suspended in 0.9 ml of anisole and 30 ml of hydrogen fluoride are condensed on the suspension at −80° C. in a teflon reaction vessel. It is stirred at 0° C. for 45 minutes and hydrogen fluoride is distilled off. To the residual anisole solution absolute ether is added and the precipitated substance is filtered after standing for one hour, washed with more portions of ether and dried over sodium hydroxide.

Yield: 220 mg (85%).
Melting point: 169° to 181° C.
$[\alpha]_D = -0.37$ (c=0.5, H₂O).
$R_f^1 = 0.5$; $R_f^2 = 0.1$; $R_f^6 = 0$; $R_f^8 = 0.45$; $R_f^{10} = 0.35$.
Amino acid analysis: Cpa 1.0, Arg 1.0, Pro 1.01, Gly 0.95, leu 1.0.

(k) Glp-His-Trp-Ser-Tyr-D-Cpa-Leu-Arg-Pro-Gly-NH₂
M: 1324.9.

36 mg (0.05 mmoles) of Glp-His-Trp-Ser-Tyr-N₂H₃ pentapeptide-hydrazide are dissolved in 1 ml of dimethyl formamide, the solution is cooled to −10° C. and 33 μl (0.2 mmoles) of a 6 n hydrochloric acid solution are added with stirring. The temperature of the mixture is kept at −10° C. while a concentrated aqueous solution of 3.8 mg (0.055 mmoles) of sodium nitrite is added with stirring and the mixture is stirred for another 10 minutes between −5° and −10° C. Thereafter to the azide solution prepared as described above a cooled solution of 35.3 mg (0.055 mmoles) of D-4-chlorophenyl-alanine-leucyl-arginyl-prolyl-glycineamide hydrogen fluoride in 1 ml of dimethyl formamide is added and the pH of the reaction mixture is adjusted to 7–8 with triethyl amine. It is stirred at a temperature between −5° and −10° C. for one hour and at 0° C. for one further hour and allowed to stand in a refrigerator overnight. The reaction mixture is evaporated in vacuo and the crude decapeptide obtained is purified on a Sephadex G-25 column (3×100 cm)(Pharmacia, Uppsala, Sweden) by partition chromatography, in a 15:1:4:20 mixture of butanol, propanol, acetic acid and water. 5-ml fractions are collected and the elution is monitored by u.v. absorption or thin layer chromatography. The fractions containing the desired material are lyophilized. The lyophilization is repeated from dilute acetic acid.

Yield: 33 mg (50%).
$R_f^1 = 0.5$, $R_f^8 = 0.55$, $R_f^{100} = 0.10$, $R_f^{12} = 0.66$.

Amino acid analysis: Glp 0.155, His 0.140, Ser 0.148, Tyr 0.105, Leu 0.200, Arg 0.135, Gly 0.170, Pro could not be calculated.

EXAMPLE 2

The preparation of D-Thx⁶-gonadoliberin (a) BOC-D-Thx-Leu-Arg-Pro-Gly-NH₂
M: 1300.5.

87.7 mg (0.1 mmoles) of BOC-D-Thx are dissolved in 1 ml of dimethyl formamide, 50 mg (0.11 mmoles) of Leu-Arg-Pro-Gly-NH₂.HF and 15 μl (0.11 mmoles) of triethyl amine are added, the reaction mixture is cooled to 0° C. and a solution of 84.5 mg (0.11 mmoles) of F-complex

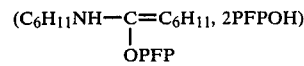

in dimethyl formamide is added. It is stirred at 0° C. for one hour and at room temperature overnight. It is then evaporated in vacuo, triturated with ethyl acetate, filtered and chromatographed on a silica gel plate (1 cm×15 cm). The column is equilibrated with a 120:6:11:20 mixture of ethyl acetate, pyridine, acetic acid and water and the desired material is eluted with this solvent mixture. About 2-ml fractions are collected in every 15 minutes. The fractions having the same $R_f$-value are combined, evaporated in vacuo, triturated with ether, filtered and dried.

Yield: 32 mg.
Melting point: 208° C. (decomp.)
$[\alpha]_D^{20} = -6.8$ (c=0.5, DMF).
$R_f^2 = 0.35$, $R_f^8 = 0.7$, $R_f^9 = 0.6$.

(b) H-D-Thx-Leu-Arg-Pro-Gly-NH₂.HCl
M: 1236.9.

50 mg of a protected pentapeptide according to step (a) are dissolved in 5 ml of glacial acetic acid and 1 ml of a 1M solution of hydrochloric acid in glacial acetic acid is added. It is stirred at room temperature. After 4 hours the reaction is complete. The title material is precipitated with ether, filtered and dried in an exsiccator, over sodium hydroxide.

Yield: 40 mg (90%).
$R_f^2 = 0.16$, $R_f^8 = 0.67$.

(c) Glp-His-Trp-Ser-Tyr-D-Thx-Leu-Arg-Pro-Gly-NH₂
M: 1860.2.

28.7 mg (0.04 mmoles) of Glp-His-Trp-Ser-Tyr-N₂H₃ pentapeptide-hydrazide are dissolved in 1 ml of dimethyl formamide and the solution is cooled to −10° C.

and 26 μl of a 6 n hydrochloric acid solutions are added with stirring. The temperature of the mixture is kept at −10° C. and a concentrated aqueous solution of 3 mg of sodium nitrite is added with stirring, and the mixture is stirred at a temperature between −5° and −10° C. for another 10 minutes. To the azide solution obtained a cooled solution of 49.5 mg (0.044 mmoles) of H-D-Thx-Leu-Arg-Pro-Gly-NH$_2$.HCl in 1 ml of dimethyl formamide is added, and the pH of the reaction mixture is adjusted to 7-8 with triethyl amine. The mixture is stirred at −5° to −10° C. for one hour and at 0° C. for another one hour and is then allowed to stand in a refrigerator overnight. The mixture is evaporated in vacuo. The residual crude decapeptide is purified on a Sephadex G-25 column (3×100 cm) by partition chromatography, in a 15:1:4:20 mixture of butanol, propanol, acetic acid and water. 5-ml fractions are collected and the elution is monitored by u.v. absorption or thin layer chromatography. The fractions containing the title product are lyophilized. Lyophilization is repeated from dilute acetic acid.

Yield: 18.7 mg (25%).
$R_f^1 = 0.65$, $R_f^8 = 0.68$, $R_f^{11} = 0.30$, $R_f^{12} = 0.81$.

EXAMPLE 3

Preparation of injections for intramuscular, subcutaneous or intravenous administration (a) The gonadoliberin derivative of the formula (I) is dissolved in distilled water, a physiological saline solution or buffered aqueous solution, in a concentration of 1 to 10 mg/ml. The solution is filtered to sterile, small portions containing 50-500 μg of active ingredient which are filled into ampoules and lyophilized, and the ampoules are sealed. The active ingredient content of the ampoules is freshly dissolved before treatment by adding 1-10 ml of distilled water and a volume, corresponding to the desired dose is administered.

(b) 20-500 μg/ml of a gonadoliberin derivative of the formula (I) are dissolved in an aqueous solution containing 0.9% of NaCl and 0.9% of benzyl alcohol. The solution is sterilized by filtration, 50-500-μg active ingredient-containing portions are filled into ampoules which are then sealed. The solutions obtained can directly be injected.

We claim:
1. A compound of the Formula (I)

Glp-His-Trp-Ser-Tyr-X-Leu-Arg-Pro-Y    (I)

wherein
  X represents a D-thyroxyl or D-thyronyl group, and
  Y stands for a glycine-amide group or an —NH-alkyl group containing 1 to 4 carbon atoms in the alkyl moiety, or a pharmaceutically acceptable acid addition salt or metal complex thereof.

2. The compound of the Formula (I) defined in claim 1 which is

Glp-His-Trp-Ser-Tyr-D-Thy-Leu-Arg-Pro-Gly-NH$_2$ or a pharmaceutically acceptable acid addition salt or metal complex thereof.

3. The compound of the Formula (I) defined in claim 1 which is

Glp-His-Trp-Ser-Tyr-D-Thx-Leu-Arg-Pro-Gly-NH$_2$ or a pharmaceutically acceptable acid addition salt or metal complex thereof.

4. A pharmaceutical composition possessing lutenizing and follicus stimulating hormone releasing activity which comprises as an active ingredient a pharmaceutically effective amount of at least one compound of the Formula (I) as defined in claim 1, or a pharmaceutically acceptable acid addition salt or metal complex thereof, in admixture with a solid or liquid carrier or additive conventionally used in the preparation of a pharmaceutical composition.

5. The pharmaceutical composition defined in claim 4 in the form of tablets, dragees, capsules, suppositories, injection solutions or nasal sprays.

6. A lutenizing and follicus stimulating hormone releasing method of treatment which comprises the step of administering to a patient in need of said treatment a pharmaceutically effective amount of the compound defined in claim 1.

* * * * *